(12) United States Patent
Echt et al.

(10) Patent No.: US 7,006,864 B2
(45) Date of Patent: Feb. 28, 2006

(54) METHODS AND SYSTEMS FOR VIBRATIONAL TREATMENT OF CARDIAC ARRHYTHMIAS

(75) Inventors: Debra S. Echt, Woodside, CA (US); Axel F. Brisken, Fremont, CA (US); Richard E. Riley, Palo Alto, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 0 days.

(21) Appl. No.: 10/869,776

(22) Filed: Jun. 15, 2004

(65) Prior Publication Data

US 2004/0260214 A1    Dec. 23, 2004

Related U.S. Application Data

(60) Provisional application No. 60/528,939, filed on Dec. 10, 2003, provisional application No. 60/496,184, filed on Aug. 18, 2003, provisional application No. 60/479,347, filed on Jun. 17, 2003.

(51) Int. Cl.
*A61N 1/39* (2006.01)
(52) U.S. Cl. .............................. 607/3; 607/5
(58) Field of Classification Search .................. 607/2, 607/3, 4, 5, 9; 601/2
See application file for complete search history.

(56) References Cited

U.S. PATENT DOCUMENTS

| | | | | |
|---|---|---|---|---|
| 4,265,228 A | * | 5/1981 | Zoll | ........................... 601/108 |
| 4,651,716 A | | 3/1987 | Forester et al. | |
| 5,165,403 A | | 11/1992 | Mehra | |
| 5,292,338 A | | 3/1994 | Bardy | |
| 5,433,731 A | | 7/1995 | Hoegnelid et al. | |
| 5,800,464 A | | 9/1998 | Kieval | |
| 5,871,506 A | | 2/1999 | Mower | |
| 5,935,158 A | * | 8/1999 | Holmstrom et al. | ........ 607/116 |
| 6,110,098 A | | 8/2000 | Renirie et al. | |
| 6,233,484 B1 | | 5/2001 | Ben-Haim et al. | |
| 6,330,475 B1 | | 12/2001 | Renirie et al. | |
| 6,408,205 B1 | * | 6/2002 | Renirie et al. | .................. 607/5 |
| 6,439,236 B1 | | 8/2002 | Porter et al. | |

FOREIGN PATENT DOCUMENTS

| | | |
|---|---|---|
| WO | WO 99/061058 | 12/1999 |
| WO | WO 03/070323 | 8/2003 |
| WO | WO 03/070323 A1 | 8/2003 |

OTHER PUBLICATIONS

Bardy GH, Cappato R., Smith WM, Hood M, Rissmann WJ, Gropper CM, Ostroff H. The totally subcutaneous ICD system (The S-ICD). PACE. 2002; 24,578.

Camm AJ, Murgatroyd FD, Nonpharmaceutical treatment of atrial fibrillation. In Atrial Fibrillation. Facts from Yesterday—Ideas for tomorrow. Futura Publishing Company, Inc., Armonk, NY, 1994.

(Continued)

*Primary Examiner*—Jeffrey R. Jastrzab
(74) *Attorney, Agent, or Firm*—Townsend and Townsend and Crew LLP

(57) ABSTRACT

Methods and apparatus for cardiac pacing, cardioversion, and defibrillation rely on delivering ultrasonic and other vibrational energy to the heart, usually after the onset of an arrhythmia. A vibrational transducer assembly is implanted or applied externally so that vibrational energy can be directed toward at least a portion of the heart from an anterior or posterior aspect, typically being implanted over the ribs, over the sternum, between the ribs, beneath the ribs, or on the back.

46 Claims, 11 Drawing Sheets

OTHER PUBLICATIONS

Dalecki D, Keller BB, Carstensen EL, Neel DS, Palladino JL, Noordergraaf A. Thresholds for premature ventricular contractions in frog hearts exposed to lithotripter fields. *Ultrasound in Med. & Biol.* 1991; 17:341-346.

Dalecki D, Keller BB, Raeman CH, Carstensen EL. Effects of pulsed ultrasound on the frog heart: I. Thresholds for changes in cardiac rhythm and aortic pressure. *Ultrasound in Med. & Biol.* 1993; 19:385-390.

Dalecki D, Raeman CH, Carstensen EL. Effects of pulsed ultrasound on the frog heart: II. An investigation of heating as a potential mechanism. *Ultrasound in Med. & Biol.* 1993; 19:391-398.

Ellenbogen KA, Wood MA, Shepard RK, Clemo HF, Vaughn T, Holloman K, Dow M, Leffler J, Abeyratne A, Verness D. Detection and management of an implantable cardioverter defibrillator lead failure. *JACC.* 2003;41:73-80.

Feldman A and Bristow M. Comparison of medical therapy, resynchronization and defibrillation therapies in heart failure trial (COMPANION). Presented at ACC 2003 Late Breaking Clinical Trials.

Franz MR. Mechano-electrical feedback in ventricular myocardium. *Cardiovascular Research.* 1996; 32:15-24.

Gibbons RJ, Antman EM, Alpert JS, Gregoratos G, Hiratzka LF, Faxon DP, Jacobs AK, Fuster V, Smith SC Jr. ACC/AHA/NASPE 2002 guideline update for implantation of cardiac pacemakers and antiarrhythmia devices: a report of the American College of Cardiology/American Heart Association Task Force on Practice Guidelines (*ACC/AHA/NASPE Committee to Update the 1998 Pacemaker Guidelines*). Circulation. 2002; 106:2145-2161.

Hu H, Sachs F. Stretch-activated ion channels in the heart. *J. Mol. Cell Cardiol.* 1997; 29:1511-1523.

Kohl P, Hunter P, Noble D. Stretch-induced changes in heart rate and rhythm: clinical observations, experiments and mathematical models. *Progress in Biophysics & Molecular Biology.* 1999; 71:91-138.

Kohl P, Nesbitt AD, Cooper PJ, Lei M. Sudden cardiac death by Commotio cordis: role of mechano-electrical feedback. *Cardiovascular Research.* 2001; 50:280-289.

Lee KL, Hafley G, Fisher JD, Gold MR, Prystowsky EN, Talajic M, Josephson ME, Packer DL, Buxton AE. Effect of implantable defibrillators of arrhythmic events and mortality in the multicenter unsustained tachycardia trial. Circulation. 2002; 106:233-238.

Moss AJ, Zareba W, Hall WJ, Klein H, Wilber DJ, Cannom DS, Daubert JP, Higgins SL, Brown MW, Andrews ML. Prophylactic implantation of a defibrillator in patients with myocardial infarction and reduced ejection fraction. *N Engl J Med.* 2002; 346:877-933.

Niehaus M, Pirr J, De Sousa M, Houben R, Korte T, Eick OJ. Non-contact cardiac stimulation with locused ultrasound pulses. *PACE 2003: 26:1023.*

Nolte S, Doring JH, Frey A. Mechanically induced ventricular extrasystoles in the isolated perfused guinea-pig heart. *Arzneim.-Forsch/Drug Research. 1987; 37(11): 1025-1029.*

Reiter MJ. Effects of mechano-electrical feedback: potential arrhythmogenic influence in patients with congestive heart failure. *Cardiovascular Research.* 1996; 32:44-51.

Smailys A, Dulevicius Z, Muckus K, Dauksa K. Investigation of the possibilities of cardiac defibrillation by ultrasound. *Resuscitation.* 1981; 9:233-242.

Tacker, WA. Fibrillation causes and criteria for defibrillation. In *Defibrillation of the heart.* Tacker, WA, ed. Mosby-Year Book, Inc., St. Louis, Missouri, 1994.

The Antiarrhythmics Versus Implantable Defibrillators (AVID) Investigators: A comparison of antiarrhythmic drug therapy with implantable defibrillators in patients resuscitated from near fatal ventricular arrhythmias. *N Engl J Med* 1997;337: 1576-1583.

* cited by examiner

METHODS AND SYSTEMS FOR VIBRATIONAL TREATMENT OF CARDIAC ARRHYTHMIAS

CROSS-REFERENCES TO RELATED APPLICATIONS

The present application claims the benefit of each of the following Provisional U.S. patent applications: Ser. No. 60/528,939 filed Dec. 10, 2003; Ser. No. 60/496,184 filed Aug. 18, 2003; and Ser. No. 60/479,347 filed Jun. 17, 2003, the full disclosures of which are incorporated herein by reference.

The disclosure of the present application is also related to the following applications being filed on the same day as the present application: U.S. patent application Ser. No. 10/869,242; U.S. patent application Ser. No. 10/869,631; and U.S. patent application Ser. No. 10/869,705, the full disclosures of which are incorporated herein by reference.

BACKGROUND OF THE INVENTION

1. Field of the Invention

The present invention relates generally to medical devices and treatment methods. More particularly, the present invention relates to methods and apparatus for treating cardiac arrhythmias with vibrational energy.

Cardiac arrhythmias, including ventricular tachycardias and ventricular fibrillation, are a leading cause of morbidity and death in Western societies. A very successful technique for treating such ventricular arrhythmias is generally referred to as "ventricular cardioversion and defibrillation," where an electrical current is applied across the chest to synchronize cardiac rhythm. The use of external cardioversion and defibrillation equipment, i.e. where electrode paddles are placed externally on the chest and where relatively high currents are applied, has been very effective, but of course requires the availability of both the equipment and an operator capable of using the equipment. More recently, implantable cardioverter defibrillator (ICD) devices have come into use, which are programmed to automatically intervene after the onset of an arrhythmia. ICD's stabilize the cardiac rhythm by delivering cardioversion, defibrillation, and pacing therapies as needed. Such ICD's have been shown to improve survival and have become the standard of therapy in patients at risk. While above references have been made to ventricular arrhythmias, atrial arrhythmias are also stabilized with ICD devices.

ICD's, however, do suffer from certain disadvantages. At present, ICD designs require one or more electrical leads to be implanted on or within the heart in order to provide pacing, cardioversion and defibrillation currents. Such lead placement requires skilled personnel and subjects the patient to radiation during the implantation procedure. The implanted leads are subject to failure and may cause cardiac perforation, thrombo-occlusion, and infection. Lead failure due to fracture or insulation break has been reported to occur in a significant fraction of the patient population after several years. Present ICD's also require a relatively long time to charge capacitors, typically from 10–15 seconds, potentially delaying treatment after a potentially lethal arrhythmia is detected. Delay in treatment also requires higher energy delivery to be successful. Moreover, many patients who have received ICD's find that the electric shocks are painful, and the unpredictable nature of the ICD firing can cause anxiety and fear.

Atrial fibrillation is more common than ventricular fibrillation and tachycardia, but is not directly lethal, although it is associated with thrombus formation in the atrial appendage and has the potential for causing embolic stroke. Atrial fibrillation is characterized by rapid and disorganized activity in both the left and right atria. There is absence of atrial contraction and often atrial enlargement. The lack of coordinated atrial contraction can reduce cardiac output which can exacerbate other heart conditions. While not usually fatal, patients in atrial fibrillation may experience chest pain, fatigue, lightheadedness, and shortness of breath. The rapid and irregular heart rate and palpitations associated with atrial fibrillation can be very distressing to patients.

The treatment of atrial fibrillation is generally similar to that for ventricular fibrillation and tachycardia, i.e. electrical defibrillation. In other cases, drugs may be sufficient to convert atrial fibrillation to normal sinus rhythm.

Since atrial fibrillation is not directly lethal, episodes occur frequently, and the patients are conscious and alert, there is a significant reluctance for patients to undergo electrical defibrillation, either externally or using implantable devices. For external defibrillation, patients generally require deep sedation or general anesthesia. Although implantable atrial defibrillators have been developed, patients have found such treatment unacceptable and the device is not currently marketed.

Patients suffering from atrial fibrillation, ventricular tachycardia, and ventricular fibrillation (abnormally fast heart rhythms), typically have structural heart disease which also makes them prone to have abnormally slow or absent heart rhythms such as sinus arrest, sinus bradycardia, heart block, asystole, and the like. Moreover, the abrupt termination of abnormally fast heart rhythm is often followed by a transient period of abnormally slow or absent heart rhythm. For these reasons, both external and implanted defibrillator devices for the termination of abnormal fast heart rhythms incorporate the capability to terminate slow or absent heart rhythms, referred to as pacing. For ICD devices, such pacing capability ordinarily requires electrical leads implanted within the heart. For external devices, such pacing capability employs the delivery of transcutaneous electrical energy through chest electrodes, which is very painful, similar to the pain associated with the delivery of electrical energy for defibrillation.

For these reasons, it would be desirable to provide improved ICD's and external defibrillators which are free from some or all of the deficiencies noted above. In particular, it would be desirable to provide such ICD's and external defibrillators which do not rely on the application of electrical current in order to achieve defibrillation. It would be further desirable to provide ICD's and external defibrillators which do not require implantation of components into the heart. In particular, it would be desirable if ICD's could be implanted remote from the heart and project energy or otherwise interact with the heart without actual contact. Such ICD's should be easy to implant, have few associated complications, be able to treat with little time delay, and provide cardioversion and defibrillation without significant pain or other undesirable side effects. Additionally, it would be desirable to provide ICD's and external defibrillators for the treatment of both ventricular and atrial rhythms that are abnormally fast, slow, or absent in a manner which is more acceptable to patients than present systems. At least some of these objectives will be met by the invention as described herein below.

2. Description of the Background Art

Patents describing the treatment of arrhythmias using mechanical shock therapy include U.S. Pat. Nos. 6,439,236; 6,408,205; 6,330,475; 6,110,098; 5,433,731; and 4,651,716; as well as PCT Applications WO 03/070323 and WO 99/061058. Other patents of interest include U.S. Pat. Nos. 6,233,484; 5,800,464; 5,871,506; 5,292,338 and 5,165,403. Medical publications discussing the effects of ultrasound energy and/or mechanical action on the heart include:

The Antiarrhythmics Versus Implantable Defibrillators (AVID) Investigators: A comparison of antiarrhythmic drug therapy with implantable defibrillators in patients resuscitated from near fatal ventricular arrhythmias. *N Engl J Med* 1997; 337: 1576–1583.

Bardy G H, Cappato R., Smith W M, Hood M, Rissmann W J, Gropper C M, Ostroff H. The totally subcutaneous ICD system (The S-ICD). PACE. 2002; 24,578.

Camm A J, Murgatroyd F D, Nonpharmaceutical treatment of atrial fibrillation. In Atrial Fibrillation. Facts from Yesterday—Ideas for tomorrow. Futura Publishing Company, Inc., Armonk, N.Y., 1994.

Dalecki D, Keller B B, Raeman C H, Carstensen E L. Effects of pulsed ultrasound on the frog heart: I. Thresholds for changes in cardiac rhythm and aortic pressure. *Ultrasound in Med. & Biol.* 1993; 19:385–390.

Dalecki D, Keller B B, Carstensen E L, Neel D S, Palladino J L, Noordergraaf A. Thresholds for premature ventricular contractions in frog hearts exposed to lithotripter fields. *Ultrasound in Med. & Biol.* 1991; 17:341–346.

Dalecki D, Raeman C H, Carstensen E L. Effects of pulsed ultrasound on the frog heart: II. An investigation of heating as a potential mechanism. *Ultrasound in Med. & Biol.* 1993; 19:391–398.

Ellenbogen K A, Wood M A, Shepard R K, Clemo H F, Vaughn T, Holloman K, Dow M, Leffler J, Abeyratne A, Verness D. Detection and management of an implantable cardioverter defibrillator lead failure. *JACC*. 2003; 41:73–80.

Feldman A and Bristow M. Comparison of medical therapy, resynchronization and defibrillation therapies in heart failure trial (COMPANION). Presented at ACC 2003 Late Breaking Clinical Trials.

Franz M R. Mechano-electrical feedback in ventricular myocardium. *Cardiovascular Research*. 1996; 32:15–24.

Gibbons R J, Antman E M, Alpert J S, Gregoratos G, Hiratzka L F, Faxon D P, Jacobs A K, Fuster V, Smith SC Jr. ACC/AHA/NASPE 2002 guideline update for implantation of cardiac pacemakers and antiarrhythmia devices: a report of the American College of Cardiology/American Heart Association Task Force on Practice Guidelines (*ACC/AHA/NASPE Committee to Update the 1998 Pacemaker Guidelines*). Circulation. 2002; 106:2145–2161.

Hu H, Sachs F. Stretch-activated ion channels in the heart. *J. Mol. Cell Cardiol*. 1997; 29:1511–1523.

Kohl P, Hunter P, Noble D. Stretch-induced changes in heart rate and rhythm: clinical observations, experiments and mathematical models. *Progress in Biophysics & Molecular Biology*. 1999; 71:91–138.

Kohl P, Nesbitt A D, Cooper P J, Lei M. Sudden cardiac death by Commotio cordis: role of mechano-electrical feedback. *Cardiovascular Research*. 2001; 50:280–289.

Lee K L, Hafley G, Fisher J D, Gold M R, Prystowsky E N, Talajic M, Josephson M E, Packer D L, Buxton A E. Effect of implantable defibrillators of arrhythmic events and mortality in the multicenter unsustained tachycardia trial. Circulation. 2002; 106:233–238.

Moss A J, Zareba W, Hall W J, Klein H, Wilber D J, Cannom D S, Daubert J P, Higgins S L, Brown M W, Andrews M L. Prophylactic implantation of a defibrillator in patients with myocardial infarction and reduced ejection fraction. *N Engl J Med*. 2002; 346:877–933.

Niehaus M, Pirr J, De Sousa M, Houben R, Korte T, Eick O J. Non-contact cardiac stimulation with focused ultrasound pulses. *PACE* 2003: 26:1023.

Nolte S, Doring J H, Frey A. Mechanically induced ventricular extrasystoles in the isolated perfused guinea-pig heart. *Arzneim.-Forsch/Drug Research*. 1987; 37(11): 1025–1029.

Reiter M J. Effects of mechano-electrical feedback: potential arrhythmogenic influence in patients with congestive heart failure. *Cardiovascular Research*. 1996; 32:44–51.

Smailys A, Dulevicius Z, Muckus K, Dauksa K. Investigation of the possibilities of cardiac defibrillation by ultrasound. *Resuscitation*. 1981; 9:233–242.

Tacker, W A. Fibrillation causes and criteria for defibrillation. In *Defibrillation of the heart*. Tacker, W A, ed. Mosby-Year Book, Inc., St. Louis, Mo. 1994.

BRIEF SUMMARY OF THE INVENTION

The present invention relies on the delivery of controlled vibrational energy, typically ultrasonic energy, to at least a portion of the heart in order to terminate arrhythmias. The ultrasonic energy may be delivered from a distance away from the heart, often from a subcutaneous location immediately outside of the thorax. Thus, implantation of the device will be significantly simpler than implantation of conventional electrical ICD's, usually not requiring fluoroscopic guidance, and potentially implantable by cardiologists and other physicians without training in electrophysiology. Alternatively, the energy may be delivered from an external location on the anterior or posterior chest region of the patient, as described in more detail below.

The methods and devices of the present invention may be used for treating either or both ventricular or atrial arrhythmias. Arrhythmias are defined here as abnormally fast, slow, or absent heart rhythms. For the treatment of ventricular arrhythmias, including asystole, heart block, ventricular tachycardia, and ventricular fibrillation, and optionally including abnormally slow or absent atrial rhythms, the vibrational energy will be directed preferentially to the ventricular regions of the heart. Because of the anatomy of the chest and heart, energy will usually be directed to the ventricles from the anterior side of the chest or abdomen, as described in more detail below.

For the treatment of atrial arrhythmias, particularly atrial fibrillation, but including sinus arrest and sinus bradycardia, the vibrational energy will be directed preferentially to the atrial regions of the heart. Because of the different anatomy of the atrial regions, such vibrational energy can be delivered from either or both anterior and posterior regions of the chest and abdomen.

In all cases, vibrational energy delivery may be accomplished using internally implanted devices or externally applied devices, i.e., devices which deliver the vibrational energy directly to the exterior of the patient's thorax or chest.

The use of ultrasonic energy for defibrillation may require lower energy thresholds and consumption than electrical systems and therefore will not need to employ long charge time capacitors. Moreover, the ultrasound energy should not directly stimulate nerves, thereby reducing or eliminating the pain which has been associated with electrical ICD's.

While the precise mechanism by which vibrational energy results in the stabilization of arrhythmias is not known, it is presently believed that the mechanism is similar to that of electrical energy. In particular, local mechanical stimulation of the myocardial tissues resulting from the delivery of vibrational energy will result in a bio-electrical response via a mechanical-electrical feedback mechanism, i.e., the transduction of the vibrational stimulus into a bio-electrical signal. In particular, the bio-electrical stimulation is believed to occur through mechano-sensitive ion channels which exist in the heart as well as many other organs. Medical literature teaches that such ion channels may be responsible for the initiation of tachyarrhythmias in the heart, with effects on the cellular action potential or the induction of premature ventricular complexes (PVC's), tachycardia, and fibrillation.

There are believed to be two potential mechanisms by which vibrational energy applied according to the methods of the present invention may stabilize cardiac arrhythmias. First, stimulation of mechano-sensitive ion channels may directly affect electrogenic currents. A second, but less likely mechanism, would rely on indirect effects by changing the flux of specific ion channels.

In a first aspect of the present invention, methods for stabilizing cardiac arrhythmias comprise detecting an onset of an arrhythmia in a patient's heart and delivering controlled vibrational energy from a vibrational transducer to the heart under conditions which terminate the arrhythmia. The delivery of ultrasound energy is usually performed using an implanted vibrational transducer, but may in some instances be performed using an external vibrational transducer adapted to deliver ultrasound energy under the conditions described below toward at least a portion of the heart.

The preferred implantable vibrational transducers which direct vibrational energy to the ventricular regions of the heart for treatment of ventricular arrhythmias may be implanted at least partially over the patient's ribs, or at least partially within a gap between the patient's ribs, or at least partially under the patient's ribs, or in the abdomen. When implanted in a gap between the ribs, the gap will likely be the natural intercostal space, but could alternatively result from removal of one or more ribs to define the implantation space. When implanted in the abdomen, the implantable vibrational transducers may be either within or outside of the peritoneal cavity.

The devices and methods described thus far for the treatment of ventricular arrhythmias will generally be suitable for the treatment of atrial arrhythmias as well. Patients with arrhythmias that are not directly fatal, and/or patients under direct medical supervision, may be treated with external devices and/or under manual control by the patient or a treating physician or other personnel. Thus, it will be possible to use more simple apparatus which do not necessarily include controls for automatic detection and firing of the vibrational transducer based automatic detection of an arrhythmia event. With such external systems, the apparatus may be placed anteriorly and/or posteriorly on the chest in order to effectively direct the vibrational energy to the atrial or ventricular regions of the heart. Similarly, the vibrational transducers may be implanted on either or both of the anterior or posterior sides of the heart in order to direct the vibrational energy at the atria or ventricles. Exemplary implantation sites are described in more detail below.

Delivery of the vibrational energy for the treatment of either or both ventricular and atrial arrhythmias may comprise activating a single piezo-electric transducer element, activating a piezo-composite material, sequentially activating individual vibrational transducer segments, sweeping a phased beam of vibrational energy across the tissue in a short time period, or the like. The nature of the vibrational energy is set forth in detail below, but will usually have a frequency in the range from 0.02 to 10 MHz, a burst length less than 5,000 cycles, a burst rate less than 100 kHz, a duty cycle less than 50%, a mechanical index less than 50, and a thermal index less than 4. Usually, for the treatment of atrial and/or ventricular fibrillation, the vibrational energy will be delivered to at least 50% of the muscle mass of the heart, preferably at least 75% of the muscle mass of the heart, and often at least 90% of the muscle mass of the heart. Usually, for the pacing treatment of asystole or bradycardia, the vibrational energy will be delivered to less than 50% of the muscle mass of the heart.

In a second aspect of the present invention, systems for stabilizing cardiac arrhythmias comprise a vibrational transducer and control circuitry for detecting the onset of an arrhythmia in the heart and for activating the vibrational transducer. The vibrational transducer is preferably implantable in a patient in the subcutaneous space near the patient's heart, and the control circuitry is adapted to cause the transducer to deliver controlled vibrational energy, usually ultrasonic energy, to the heart under conditions which terminate the arrhythmia. Such conditions were described generally above in connection with the methods of the present invention.

The vibrational transducer and control circuitry will usually be packaged in a common housing, but in some instances may be packaged separately in separate implantable housings, and typically connected by a cable.

The vibrational transducer may comprise any of the structures described above, and the transducer will operate under the conditions described above. The control circuitry will typically comprise ECG elements or other conventional circuitry for detecting onset of an arrhythmia, and will usually further comprise a signal generator for the transducer, a power amplifier, and an impedance matching circuit, optionally including multiple such circuits for multiply segmented transducers. Usually, the circuitry will further comprise a battery or a remotely rechargeable battery, such as a battery which may be recharged using radiofrequency transmissions. Usually, the control circuitry will further be adapted to communicate with an external transmitter and receiver for communications, including both patient data retrieval and programming and control of the control circuitry.

BRIEF DESCRIPTION OF THE DRAWINGS

FIG. 1A shows the pulse repetition period (PRP) and FIG. 1B illustrates a single pulse in more detail.

DETAILED DESCRIPTION OF THE INVENTION

The present invention relies on directing vibrational energy, particularly ultrasound energy, into cardiac tissue in order to terminate an arrhythmia. An understanding of the nature of ultrasound energy and biological tissue is of use.

Figure 1A:
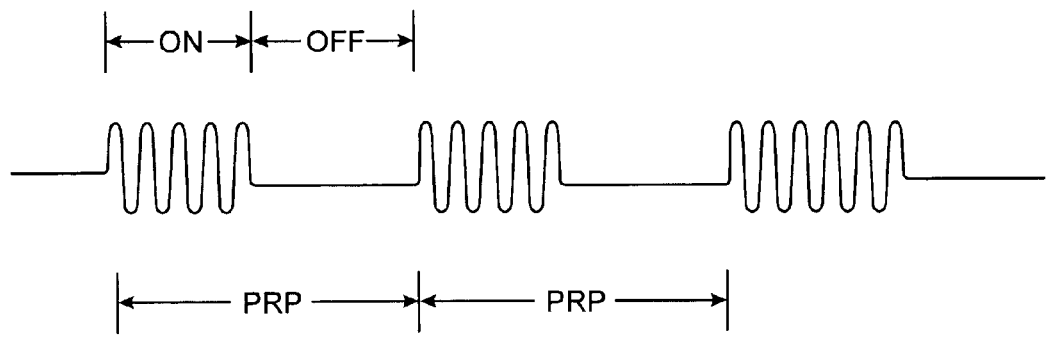
FIGS. 1A and 1B are a schematic illustrations of a longitudinal vibrational wave traveling through biological tissue.
Figure 1B:
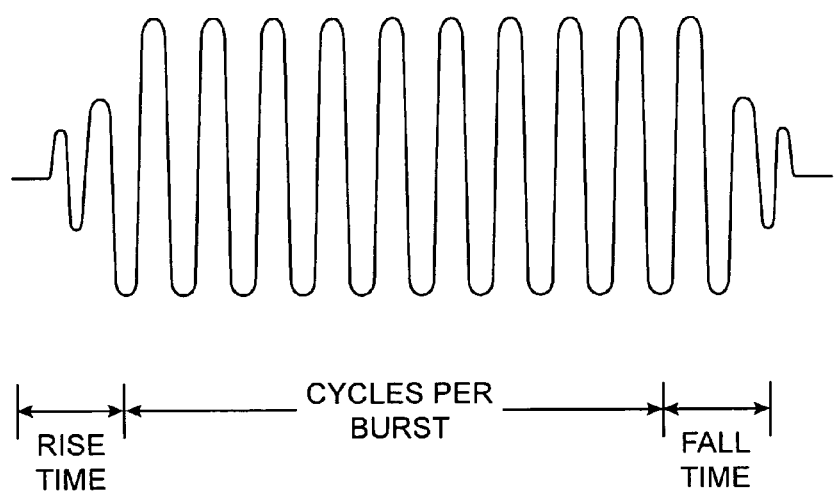

Ultrasound in biological tissues is virtually exclusively a longitudinal traveling wave, as illustrated in FIGS 1A and 1B. The wave travels at typically 1.5 millimeters per microsecond, in a straight line unless reflected or refracted. Ultrasound may be CW (continuous wave), meaning it is on all the time, or burst mode, comprising periods of ON time separated by lengths of OFF time (FIG. 1A). The lengths of the ON and OFF periods may be the same or different, and the total of the "on time" and "off time" is referred to as the pulse repetition period (PRP). As illustrated in FIG. 1B, ultrasound waves do not come up to peak amplitude instantaneously. The number of cycles involved in the rise time and the fall time are approximately equal to the Q (quality factor) of the device. The period of an ultrasound wave is the time for one complete cycle. The reciprocal of period is the frequency. Bursts may occur at any selected frequency. The burst rate is defined as the pulse repetition frequency (PRF), which is the reciprocal of the pulse repetition period (1/PRP). The amplitude of the wave can be defined in terms of pressure. In power applications, the magnitude of peak positive pressure is usually greater than that of the peak negative pressure. The waveform is slightly asymmetric due to non-linearities. These non-linearities arise from different velocities of sound in the body as a function of signal strength, and are dependent on the distance of travel through tissue and of course, amplitude.

From the above basic descriptors, other ultrasound parameters follow. The duty cycle is defined as the percent of time the ultrasound is in the ON state. Thus, a continuous wave would have a duty cycle of 100 percent. Intensity is the ultrasound power per unit area. Further common definitions are Ispta (intensity, spatial peak temporal average), the average intensity in the center of the beam over all time, and Isppa (intensity, spatial peak pulse average), the average intensity in the center of the beam averaged only over the duration of the pulse.

Two additional parameters are the Mechanical Index (MI) and the Thermal Index (TI). MI is defined as the peak negative pressure in units of MPa divided by the square root of frequency in units of MHz. The parameter is defined for diagnostic ultrasound and reflects the ability of ultrasound to cause mechanical damage, across a wide range of frequencies. The FDA guideline for diagnostic ultrasound allows a maximum MI=1.9. TI for soft tissues is defined as the average power in the beam in milliwatts times the frequency in MHz divided by 210. TI defines the capability of ultrasound to create thermal bioeffect in tissue, and a value of unity corresponds to a theoretical temperature rise in normal tissue of one Centigrade degree. These expressions show important trends for ultrasound. For a given pressure, lower frequencies tend to result in greater mechanical bioeffects. Further, for higher frequencies, there is a stronger tendency for greater thermal bioeffects.

An ultrasound beam is attenuated by the tissues through which it propagates. Tissue motion has no effect on ultrasound attenuation. At frequencies below 5 MHz, attenuation in blood is negligible. Attenuation in myocardium, muscle, fat, and skin is approximately 0.3 dB per MHz per centimeter of propagation path. Consequently, a 1 MHz beam will suffer little attenuation through the body wall and heart. All frequencies of ultrasound do not propagate well through air; it is virtually totally attenuated. Gases in the lungs and bowel essentially totally obstruct the beam. Attenuation in bone is strongly frequency-dependent. The attenuation at 1 MHz is in excess of 12 dB, rising almost linearly with frequency. At 100 kHz, attenuation is negligible.

Figure 3:
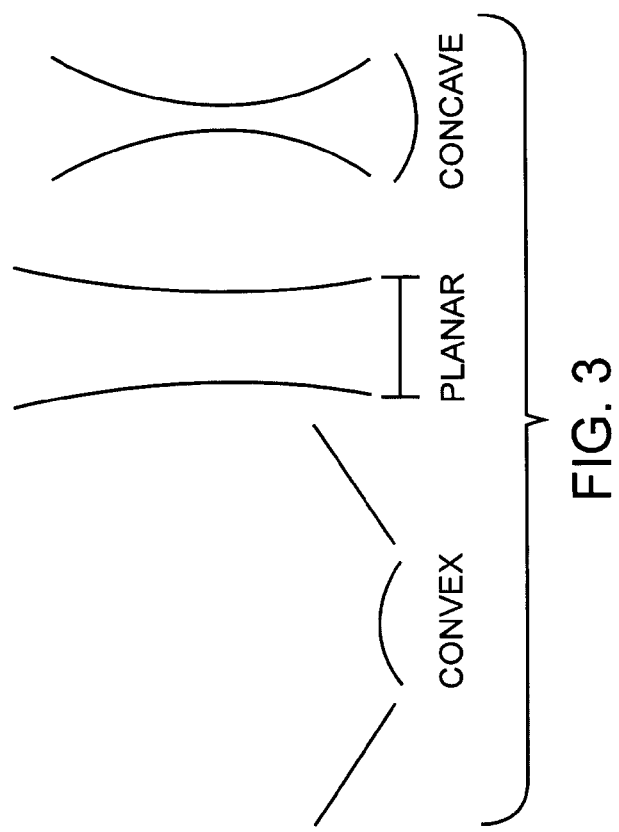
FIG. 3 illustrates high frequency beams from convex, flat, and concave apertures which form divergent, mildly focused, and sharply focused beams, respectively.
Figure 2:
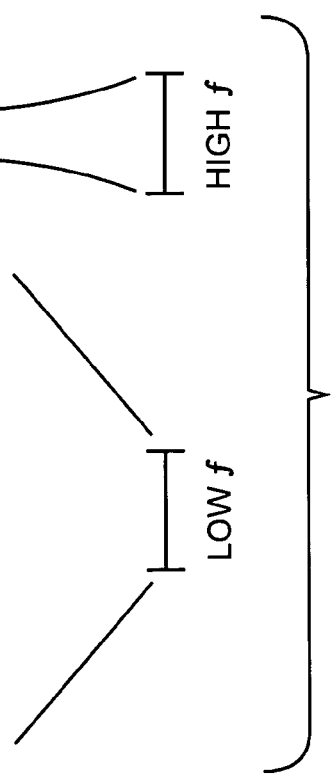
FIG. 2 is a schematic illustration of the relationship between frequency (wavelength) and focus of an ultrasonic beam.

Ultrasonic beams are highly dependent on the aperture of the radiator and the frequency, and whether the beam is continuous wave or burst mode (pulsed). A simple rule is that in the far field, the beam width is given by the wavelength divided by the aperture. Given the same sized apertures, a low frequency (Low f) beam might be almost isotropic (equal intensity in all directions) while a high frequency (High f) beam will be focused, as illustrated in FIG. 2. Further, the shape of the aperture will affect the beam. FIG. 3 depicts high frequency beams from convex, planar, and concave apertures, forming divergent, mildly focused, and sharply focused beams, respectively. In the far field, pulsed and continuous beams have approximately the same profiles. In the near field, however, continuous beams are characterized by multiple peaks and valleys due to constructive and destructive interference, respectively, of wavefronts from across the aperture. For short bursts of ultrasound, constructive and destructive interference is limited to emissions from smaller portions of the aperture, and consequently, near field emission profiles are more uniform.)

Figure 4B:
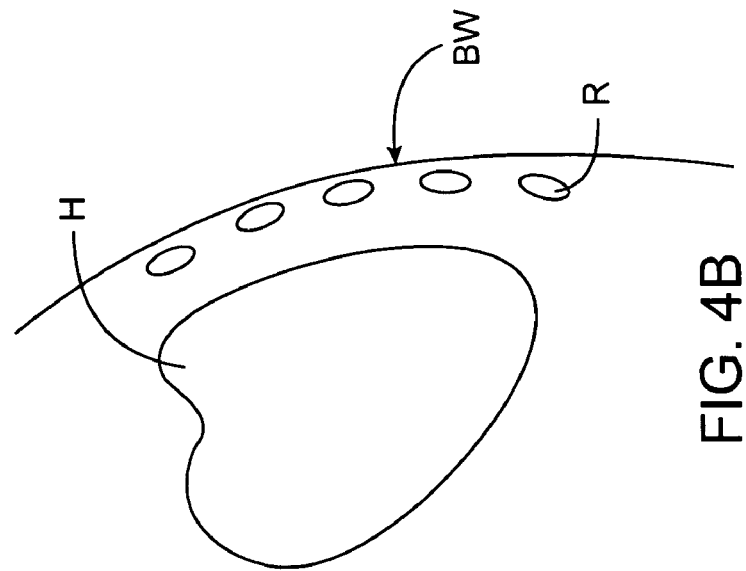
FIGS. 4A and 4B illustrate the anatomy in which the vibrational transducers of the present invention are to be implanted.
Figure 4A:
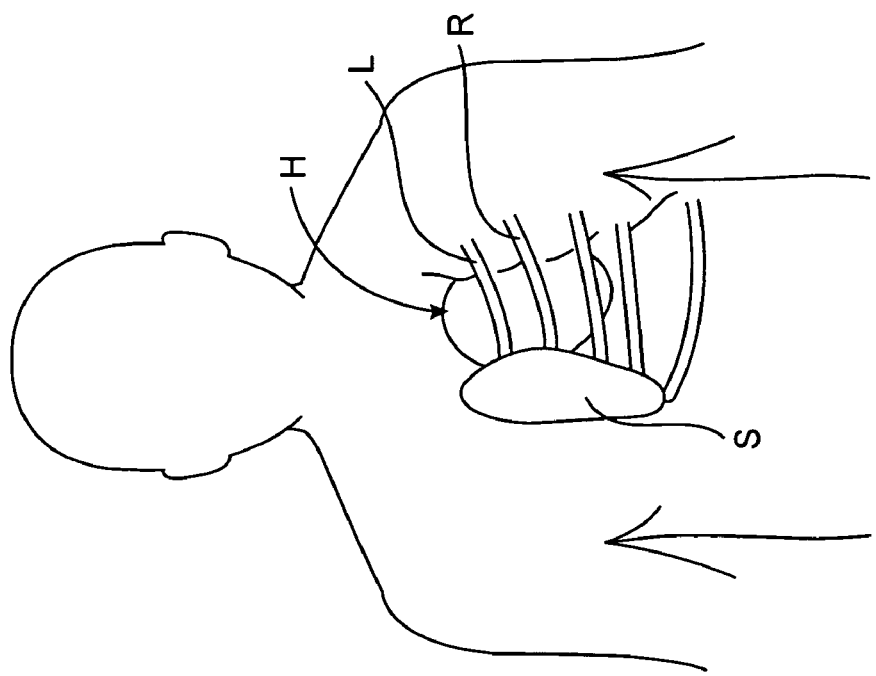

Referring now to FIGS. 4A and 4B, the present invention relies on directing ultrasound and other vibrational energy to regions of the heart H in order to stabilize cardiac electrical activity as generally discussed above. In particular, for defibrillation, it is desirable to be able to direct the ultrasonic energy over as great a portion of the heart as possible, in order to assure maximum effectiveness. Usually, for defibrillation, the present invention will provide for directing the ultrasonic energy to at least 50% of the heart, preferably at least 75%, and more preferably 90% or greater. Alternatively, it may be desirable to be able to direct the ultrasonic energy to a smaller portion e.g., less than 50% of the heart, since this can be effective for pacing. As the heart is located beneath the body wall (BW), ribs R and sternum S, however, the vibrational transducer assembly (as described in greater detail below) must be properly located to deliver the energy. Bone and cartilage significantly attenuate the propagation of high frequency ultrasonic energy, and the lungs L (which are filled with air) will totally obstruct the transmission of such energy.

Figure 5A:
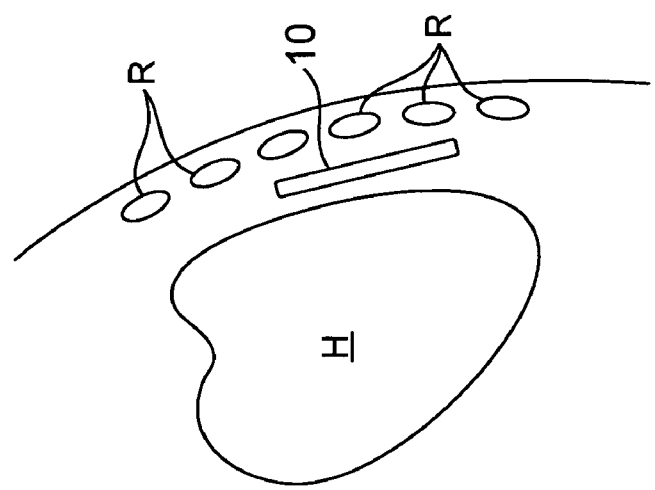
FIGS. 5A–5C illustrate alternative implantation sites for the vibrational transducers and transducer assemblies of the present invention.
Figure 5B:
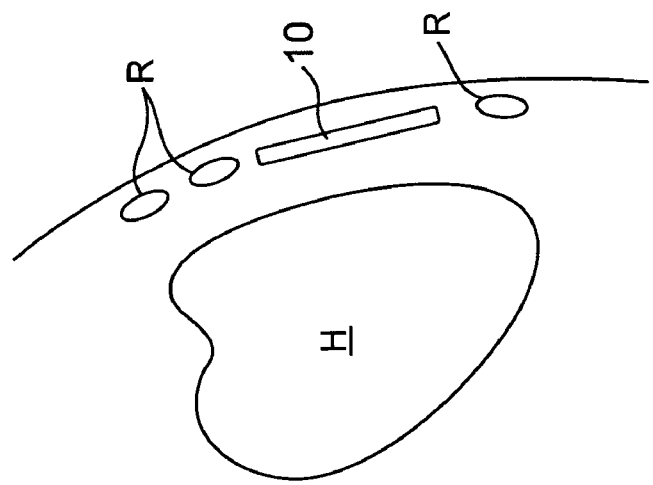
Figure 5C:
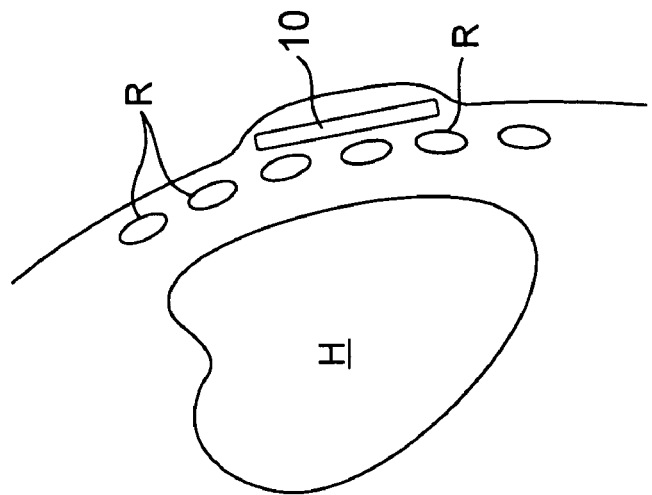

It will generally be preferred to implant a vibrational transducer assembly 10 either over the ribs R and/or sternum, as shown in FIG. 5C, between or in place of the ribs R, as shown in FIG. 5B, or perhaps less desirably under the ribs R, as shown in FIG. 5A. When implanted beneath the ribs, the vibrational transducer assembly 10 will usually be placed over or spaced slightly anteriorly from the pericardium. Alternatively, but not shown, the transducer assembly may be implanted in the abdomen, either within or outside of the peritoneal cavity.

Figure 6:
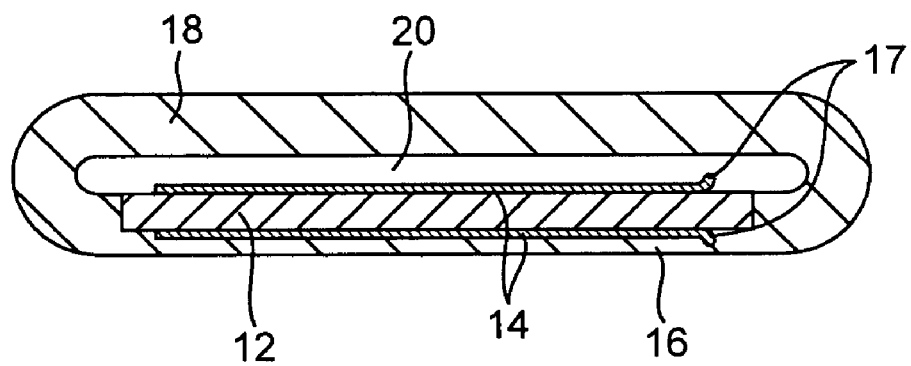
FIG. 6 illustrates a first embodiment of a vibrational transducer assembly constructed in accordance with the principles of the present invention.

Referring now to FIG. 6, a first exemplary vibrational transducer assembly 10A comprises a quarter wave front surface matched device. A half-wave thickness of piezoelectric ceramic 12 is sandwiched between thin layer electrodes 14 having leads 17 and a quarter-wave matching layer 16 disposed over the first surface. The piezoelectric ceramic 12 is positioned in a housing 18 with an air cavity 20 at its rear surface. In this way, the quarter-wave matching layer 16 provides a front surface of the assembly 10A, and the edges and back of the housing need only be strong enough to provide mechanical support. The air cavity 20 will typically have a width of about 1 mm, and the thickness of the ceramic and matching layer will vary depending on the desired frequency of operation. Table 1 below shows the operational frequencies and thicknesses of the ceramic layer 12 and matching layer 16.

TABLE 1

| Device Frequency (MHz) | Ceramic Thickness (mm) | Matching Thickness (mm) |
|---|---|---|
| 2.0 | 1.0 | 0.37 |
| 1.0 | 2.0 | 0.75 |
| 0.5 | 4.0 | 1.5 |
| 0.25 | 8.0 | 3.0 |
| 0.10 | 20.0 | 7.5 |

The methods of the present invention likely result from the mechanical effects of ultrasound. As such, the maximum frequency might be on the order of 1 MHz. From a structural point of view, at 0.10 MHz, the device package thickness might be on the order of 30 mm thick, probably the maximum acceptable for an implant. If the device needs to be implanted over the ribs, or placed externally, the lower frequencies are preferred. At 0.25 MHz, the attenuation due to bone might be minimal, thus suggesting an operational frequency in the 0.10 to 0.5 MHz range.

Operating below 0.25 MHz with a conventional quarter wave device may not be especially advantageous due to the higher voltages needed to drive the device. Also, as the device gets thicker, it becomes substantially heavier.

As shown, the transducer assembly 10A may be substituted with a 1–3 piezo-composite material instead of the ceramic. Piezo-composite material consists of piezoelectric ceramic posts in a polymer matrix. Such materials are thinner than the equivalent pure ceramic material needed to achieve a particular frequency and there is no need to provide a matching layer. Thus, a simple seal providing electrical insulation may be substituted for the matching layer 16 of FIG. 6. Suitable thicknesses for the piezo-composite material are shown in Table 2 below.

TABLE 2

| Device Frequency (MHz) | Piezo-composite Thickness (mm) |
|---|---|
| 2.0 | 0.75 |
| 1.0 | 1.5 |
| 0.5 | 3.0 |
| 0.25 | 6.0 |
| 0.10 | 15.0 |

Besides creating a thinner package, the piezo-composite materials have another significant benefit in that they can be easily curved, potentially to conform to anatomical features or to optimize the transducer beam profile. It must be remembered that any curvature will affect the focal characteristics of the device.

Figure 7:
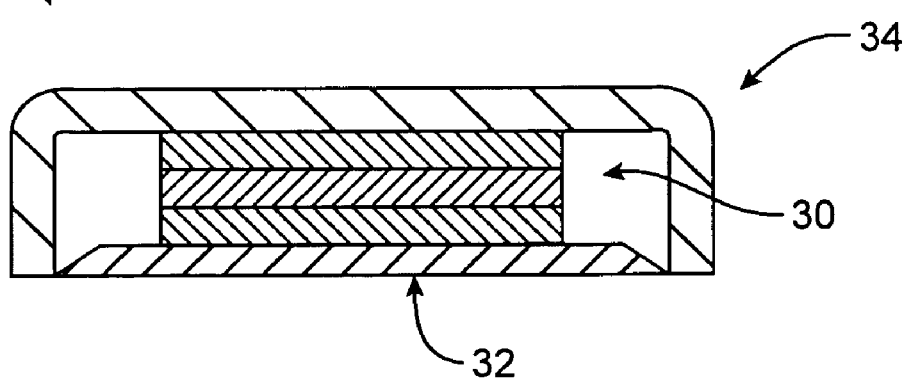
FIG. 7 illustrates a second embodiment of a vibrational transducer assembly constructed in accordance with the principles of the present invention.

Referring now to FIG. 7, a vibrational transducer assembly 10B may be formed as a variation on a Tonpilz transducer where a piezo drive 30 (shown as a stack of piezoelectric material) induces ultrasonic vibration in a front vibrator 32. The package 34 provides the necessary tail mass for operation of the transducer assembly. Optionally, a structure (not shown) for retaining the front surface vibrator 32 against the ceramic stack 30 and housing 34 may be provided. Strong vibrations of the surface vibrator may exceed the tensile strength of the ceramic and/or bonding material. Such transducer assemblies are particularly well suited to operation at low frequencies of 0.1 MHz and below.

For defibrillation, the device of the present invention will require an aperture generating a relatively wide acoustic beam in order to deliver ultrasonic or other vibrational energy over a relatively large portion of the heart. Due to biological constraints, the transducer will always be in close proximity to the heart, and as such, the heart may be in the near field of the acoustic beam. With typical human heart dimensions of 12 cm in length and 10 cm in width, the ultrasonic or other vibrational energy aperture will typically be circular with a diameter on the order of 10 cm, more preferably elliptical with long and short axes of 12 and 10 cm, and most preferably elliptical with the ultrasonic or other vibrational energy aperture slightly exceeding the dimensions of the heart to assure maximal coverage of myocardium with therapeutic energy. It is recognized that many different sizes of devices might be required to meet the needs of different patient sizes.

Figure 8:
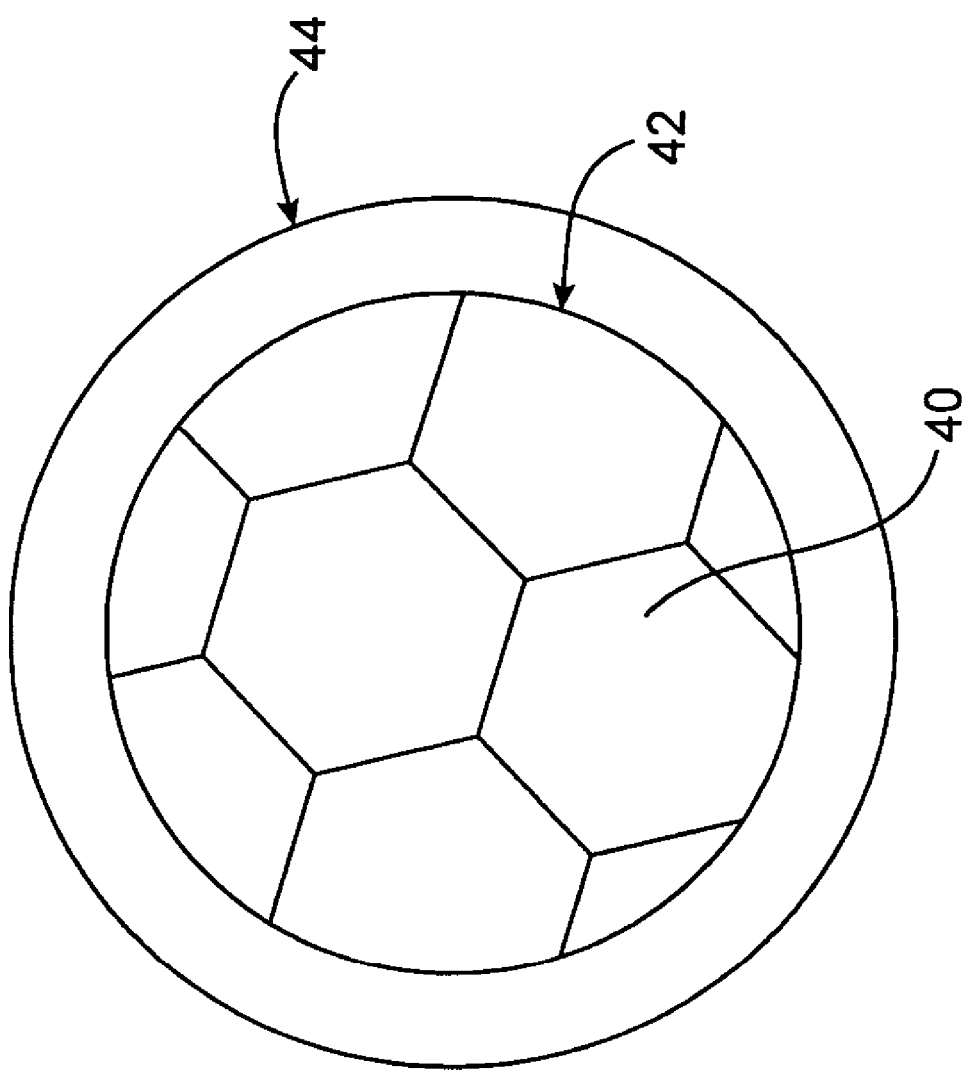
FIG. 8 illustrates a third embodiment of a vibrational transducer assembly constructed in accordance with the principles of the present invention.

Further variations on device design are possible. Specifically, recently developed high strain materials such as single crystal or polymer piezoelectrics might be employed. In the case of the single crystals, current technology does not provide material with dimensions consistent with the sizes projected to cover a significant fraction of the heart. Consequently, a mosaic structure of individual pieces or sections 40 of piezo electric material, as depicted in FIG. 8 might be employed. The sections 40 are arranged within an ultrasonic radiative aperture 42 in a casing 44. The sizes of individual pieces would be consistent with current manufacturing technology, currently approximately one inch on the side. The single crystals may have individual signal generators, driving amplifiers, and/or impedance matching circuits for parallel or serial operation. Alternatively, the single crystals may be driven in a sequential (multiplexed) manner by a single signal generator, power amplifier, and matching circuit. The single crystals may employ front surface impedance matching (quarter wave thicknesses) as used for the conventional piezoelectrics as depicted in FIG. 6. The mosaic of individual pieces may be mounted on a flat coplanar surface, or the devices might be so mounted as to give the front surface of the device either a concave or convex surface for better implantation under the patient's skin. Likewise, the polymer devices might be flat or curved, as appropriate for acoustic coupling beneath the patient's skin. Polymer devices probably will not require a front surface impedance matching layer, but may be backed with a high impedance backing layer to project as much of the acoustic energy out into the patient as possible. Driving materials for transducers may also include any other electromechanical material, one specific example being magnetostrictive materials.

The device may be driven with a high voltage and a high current. After appropriate electrical impedance matching, the current drain on the battery may exceed the capability of the same. It is thus proposed to segment the aperture into multiple individual pieces of piezoelectric, as depicted in FIG. 8 and as described above. In this case, each element may be driven by an individual power amplifier, impedance matching circuit, and signal generator (or a signal generator gated to individual devices). Alternatively, the single crystals may be driven in a sequential (multiplexed) manner by a single generator, power amplifier, and matching circuit. As such then, exposure of the heart would be segmental. If, for example, the aperture consisted of 10 elements, operating with 5 cycles at 1 MHz, each element might be triggered every 50 microseconds, allowing for an effective 10 percent duty cycle. This would reduce the peak current demand on the battery by a factor of 10.

Figure 9B:
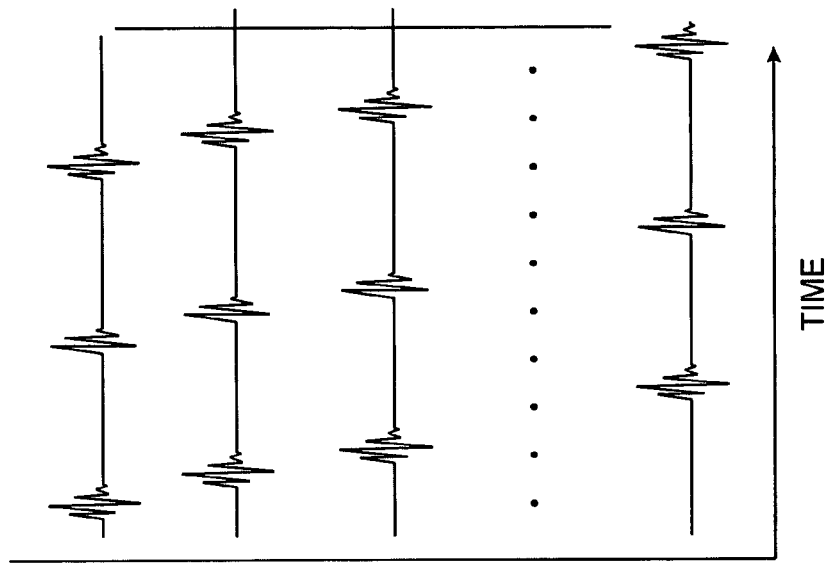
FIGS. 9A and 9B illustrate a circuit configuration (FIG. 9A) and serial burst pattern (FIG. 9B) which would be suitable for operating the vibrational transducer assembly of FIG. 8.
Figure 9A:
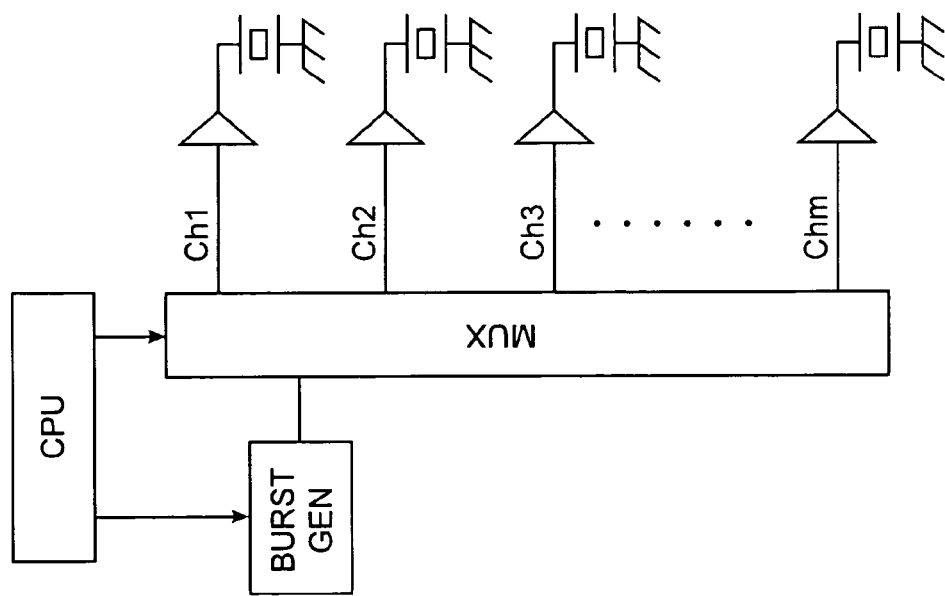

FIGS. 9A and 9B depict one possible circuit configuration for generating serial bursts from the segmented aperture, and further depicts the interlaced output from each of the individual elements within the aperture. It is possible to generate multiple bursts from every element during a small fraction of the cardiac cycle. The myocardium will effectively experience simultaneous ultrasound exposure. Care must be exercised in the implementation of this concept to prevent excessive beam spreading from the smaller elements and loss of far field signal strength. Low frequency devices would be more prone to this problem than high frequency devices.

Alternatively, the segmented aperture of individual elements of electro mechanical material, or clusters of one to several posts of a piezo composite material, may be driven in a phased sequence, so as to create an ultrasound beam in one of several particular directions. "Phasing" means that the driving signals applied to all elements or segments of the aperture have time delays such that the wavefronts from each element or segment arrive at a designated tissue mass at the same time (constructive interference). Although the amplitude in this tissue mass will be greater due to the focusing effect of the phased aperture, the beam may no longer cover the entire region of tissue requiring treatment. Consequently, in rapid succession, on time scales very small compared to the time of the cardiac cycle, the beam may be directed to multiple tissue masses in the region of treatment, so as to effectively uniformly expose the entire region with ultrasound.

Circuit configurations for operation in a phased array mode may be quite similar to the circuit configuration depicted in FIG. 9A. For phased array operation, all elements would be operative at the same time, albeit with different time delays. The burst generator would provide the different time delays which would be directed to specific amplifiers/elements through the multiplexer (MUX). Multiple sets of time delays would result in beams in multiple directions.

Instead of segmenting the aperture in a compact two-dimensional format, the aperture may be comprised of a series of segments or elements in a linear arrangement. Such an array of elements may be implanted or fixed externally for directing vibrational energy to the heart from between the ribs. Indeed, a second string of elements could be implemented in similar format, for directing vibrational energy to the heart through another intercostal space, either above or below the first string of elements. Alternatively or in conjunction, a string of elements may be implemented over the sternum. Although there will be some attenuation of the ultrasonic beam, directing vibrational energy through the sternum will assure a pathway to the heart unimpeded by lung tissue. The single or multiple linear strands of aperture segments or elements can be electrically driven in parallel or serial format, or driven in a phased format for targeting of a specific region of the heart or for sweeping the ultrasonic beam across a greater portion of the heart.

For pacing therapy, the device of the present invention may not require an aperture for generating a wide acoustic beam since it is not necessary for the acoustic beam to deliver energy to the majority of the heart. Thus, pacing may be accomplished by delivering vibrational energy from a portion of the transducer aperture using a segmental design, or alternatively, from a separate transducer aperture generating a narrower acoustic beam. If using a separate transducer, the separate transducer may be smaller in size and of a different shape. Thus, the invention may be comprised of one or more that one transducer assembly, connected by a cable (not illustrated).

It is assumed that the desired effect is a mechanical effect. Operating a transducer in continuous wave mode creates a maximum thermal effect and a minimal mechanical effect. Operating in a burst mode with a low duty cycle and a high amplitude minimizes thermal effects and maximizes mechanical effects. It is further believed, with some empirical evidence, that high burst rates (and short burst lengths) provide the yet further enhancements to a mechanical effect. Consequently, a preferred design will be for shortest possible burst lengths, maximum amplitude, and duty cycle to the thermal limit.

The above paragraphs discussed some of the packaging considerations for the device. To summarize, the overhead on the aperture is expected to be minimal, perhaps adding 5 to 10 mm to the diameter of a device. The thickness of the device will be defined by the type and the frequency. The electronics package (and battery) can be combined with the transducer or can be separately housed, with a cable between the two units.

Figure 10:
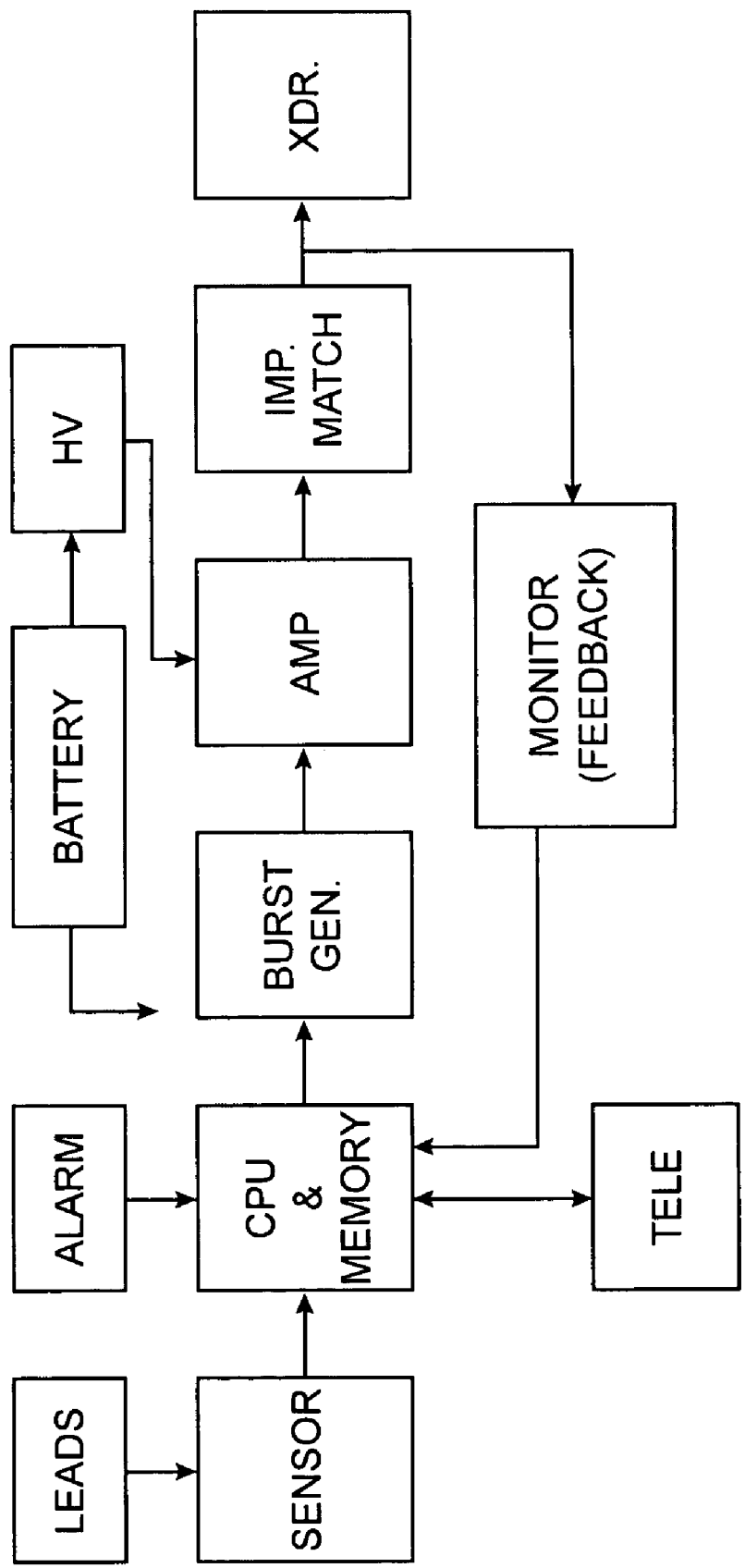
FIG. 10 is a block diagram showing an embodiment of the control circuitry implementation of the present invention.

FIG. 10 represents a block diagram of a possible electronics package. The sensor circuit would be monitoring the heart and the power side of the system would generally remain idle until such time as an arrhythmia event were to occur. The sensor circuits may be integral with the CPU. Once an event is detected, the CPU would trigger the burst generator which would generate a preprogrammed series of bursts, until such time as the heart has returned to normal rhythm. The electrical bursts would pass to a power amplifier, an impedance matching circuit, and on to the transducer. A battery would supply power for the typically digital circuits in the CPU, telemetry, sensor, and burst generator, the typically analog circuits in the front ends of the sensor and amplifier, and to a voltage converter producing the high voltage for the output stages of the amplifier. Monitoring circuitry would provide feedback to the CPU about the actual performance of the power amplifier and transducer(s).

The operational life of a defibrillation system may be on the order of a several events with durations each of a few minutes. The operational life of a pacing system may be on the order of a year or more progressing up to 5 years. A battery volume on the order of one or two commercial "D" cells is anticipated. The amplifier and impedance matching circuits might require on the order of 25 cubic centimeters of volume, and the digital portions on the order of 5 cubic centimeters. In all, it is reasonable to assume that the package could be implanted into the chest of a human. Use of a rechargeable battery system utilizing transcutaneous inductive energy transmission may be beneficial.

The circuitry of FIG. 10 may be adapted to drive the associated vibrational transducer under conditions which will impart vibrational energy to the heart so that the arrhythmia is terminated. In particular, the vibrational transducer may be operated under the conditions specified in Table 3. The device of the present invention may or may not allow for synchronization of the therapeutic ultrasound or vibrational energy burst to the cardiac cycle. In a first embodiment, once a rhythm abnormality is detected, the system will immediately initiate the preprogrammed therapeutic protocol, irrespective of the time point on the cardiac cycle. In a second embodiment, the system may trigger during any time within prespecified intervals of the cardiac cycle. In yet a third possible embodiment, the system may initially be energized for a preprogrammed protocol, but then fall into a specified time interval of the cardiac cycle as normal rhythm is detected or anticipated.

The duration that the vibrational energy is delivered as a function of the transducer frequency, burst length (number of cycles), burst rate, and duty cycle. It is anticipated that the vibrational therapy might be applied for a duration less than one complete cardiac cycle. It is further anticipated that the vibrational energy therapy might be repeated for more than one cardiac cycle.

may operate automatically similar to an implanted device. Most simply, the vibrational transducers may be incorporated into external units capable of being applied to either or both the anterior chest (FIG. 11) or posterior chest (FIG. 12). For anterior placement, the patient will usually be reclining on the table, bed, or ground; vibrational transducer 100 attached to an external generator 102 by an attaching cord 104 is applied over the patient's chest, preferably using a gel layer to enhance contact. Usually, the transducer 100 will be placed generally over the heart and the transducer may be configured to direct the energy over a specific region (e.g., the atrium or ventricle).

Alternatively or additionally, a vibrational transducer 110 may be placed beneath a reclining patient on the posterior region of the patient's chest, as illustrated in FIG. 12. The transducer 110 will also be connected to a generator 112 by a cord 114, and the placement may be chosen to direct the vibrational energy preferentially to a region of the heart.

Figure 11:
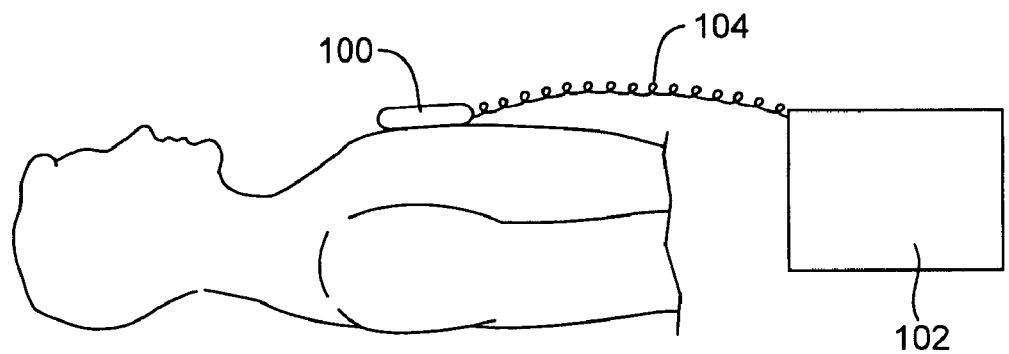
FIG. 11 illustrates the anatomic position in which a transducer of the manual invention is placed externally on the anterior chest wall.
Figure 12:
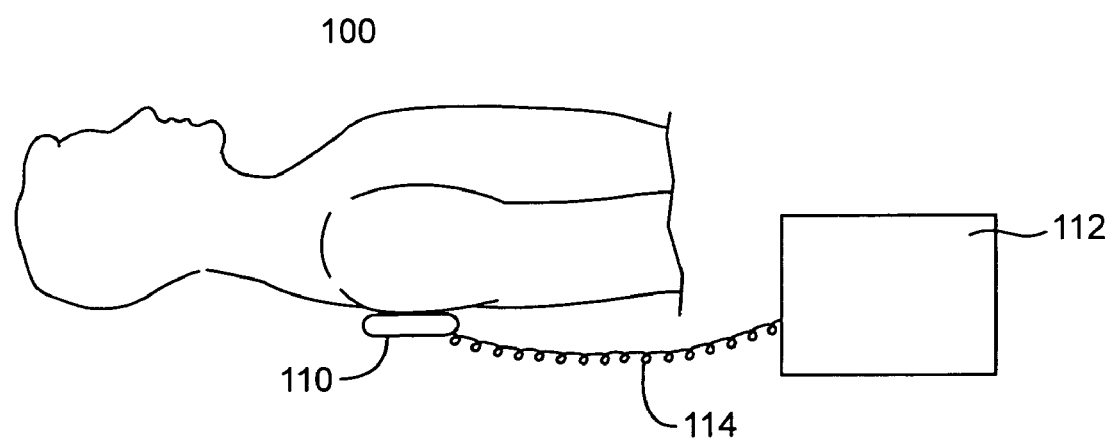
FIG. 12 illustrated the anatomic position in which a transducer of the manual invention is placed externally on the back posteriorly.

Systems embodied for external use have sensor circuitry, control circuitry, power supply, and burst generation incorporated into the generator (component 102 in FIG. 11. and 112 in FIG. 12). The ECG sensors may be incorporated into the transducer housing or optionally standard transcutaneous ECG electrodes may be connected to the body and to the generator via cables.

Figure 13A:
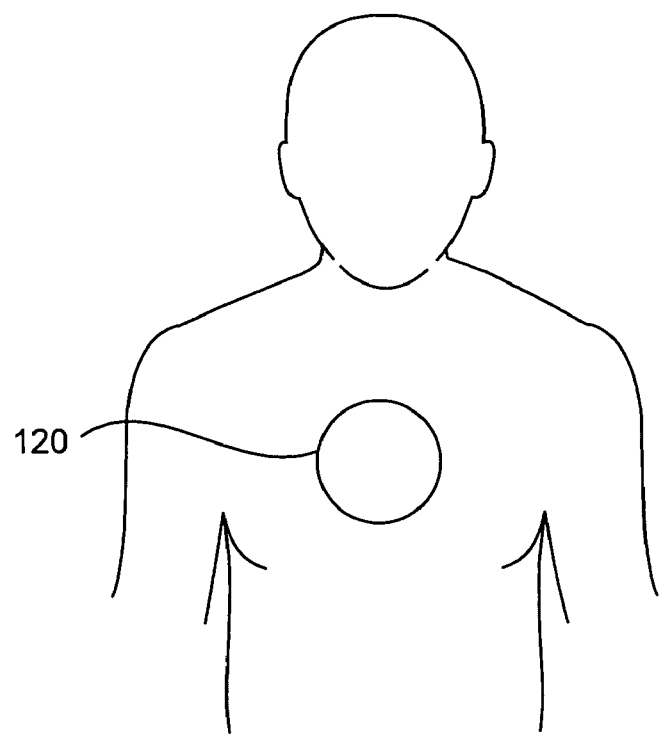
FIGS. 13A and B illustrate an implantation site for the vibrational transducers and transducer assemblies of the present invention.
Figure 13B:
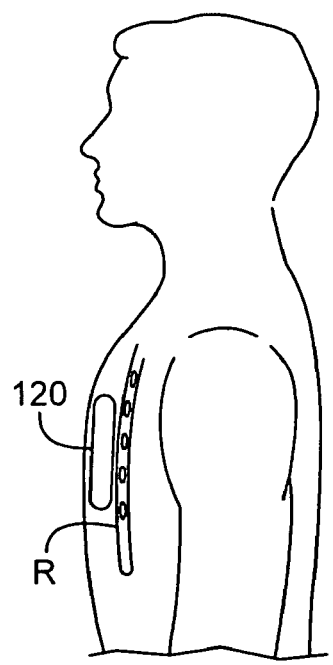

Treatment of arrhythmias may also be accomplished with one or more implanted vibrational transducers, including both automatically triggered and manually triggered transducers. The circuitry for automatic triggering of transducers has been discussed above. Manual triggering may be accomplished using an external wand, such as a radiofrequency or magnetic controller, in order to initiate operation of the transducer. For example, an implantable transducer 120 may be placed subcutaneously in an area of the anterior chest directly over the ribs R and/or sternum and preferably over the region of the heart, as shown in FIGS. 13A and 13B. Alternatively, or additionally, the vibrational transducer 130

TABLE 3

| Parameter | Cardioversion and Defibrillation | | | Pacing |
|---|---|---|---|---|
| | Preferred Implementation | More preferred Implementation | Most preferred Implementation | Most preferred Implementation |
| Frequency (MHz) | 0.020–10.0 | 0.050–1.00 | 0.100–0.300 | 0.25-0.50 |
| Burst length (cycles) | <5000 | <500 | <50 | <50 |
| Burst rate (Hz) | >10 | ≧100 | ≧100 | Single burst |
| Duty cycle (%) | <50 | <10 | <5 | 100 |
| Duration (msec) | <200 | <50 | <20 | <0.20 |
| No. of cardiac cycles | as required | <5 | <15 | All |
| MI | <50 | <25 | <15 | <2 |
| TI | <4 | <1 | <.1 | <0.1 |
| Myocardial Coverage (%) | >50 | >75 | <90 | <20 |
| Cardiac cycles from sense to trigger | <10 | <5 | <2 | 0 or 1 |

Figure 14A:
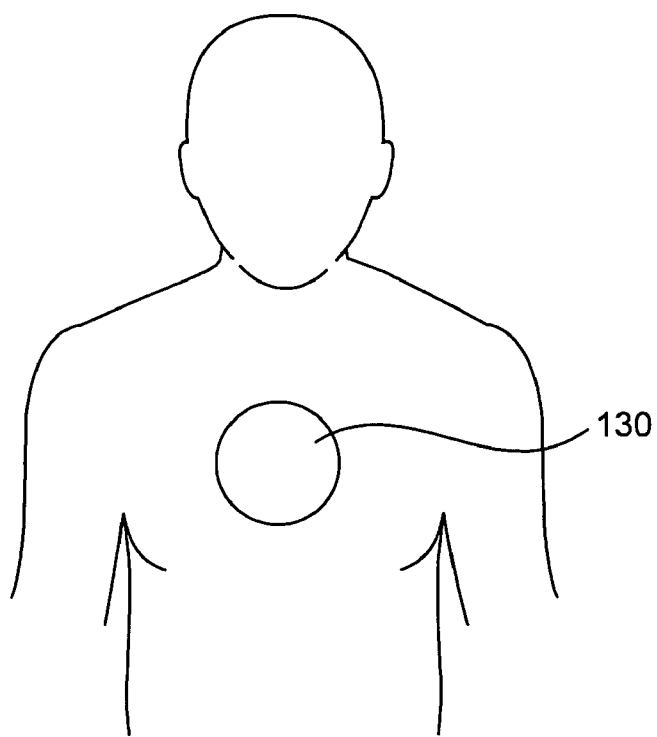
FIGS. 14A and B illustrate an alternative site in the posterior chest for the implantation of vibrational transducers and transducer assemblies of the present invention.
Figure 14B:
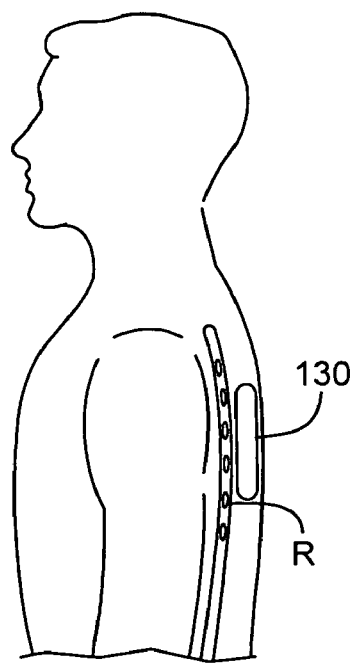

The device designs and implementations referred to thus far are generally useful for the treatment of both ventricular and atrial arrhythmias. Treatment of atrial and ventricular arrhythmias using pacing, cardioversion, or defibrillation, however, may also be accomplished with systems which may be somewhat simpler than those described above being external to the body with transducers deployed at body locations in addition to those described above. The external systems may be adapted for either manual control by either the patient or by the doctor or other medical personnel or it may be implanted subcutaneously in a posterior area of the chest, as shown in FIGS. 14A and 14B. The transducer 130 will usually be implanted over the ribs R and disposed to preferentially deliver vibrational energy to the atrial or ventricular region of the heart.

In the manually controlled embodiments of the vibrational transducers, circuitry for sensing the electrocardiogram will usually be included in order to synchronize the timing of the delivery of the vibrational energy to an appropriate point in the cardiac cycle based on detection of the ventricular QRS.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for stabilizing cardiac arrhythmias, said method comprising:
   detecting an onset of an arrhythmia in a patient's heart;
   delivering controlled vibrational energy from a vibrational transducer to the heart under conditions which terminate the arrhythmia, wherein the vibrational energy has a frequency in the range from 0.02 to 10 MHz, a burst length less than 5,000 cycles, a burst rate less than 100 kHz, a duty cycle less than 50%, a mechanical index less than 50, and a thermal index less than 4.

2. A method as in claim 1, wherein the arrhythmia is ventricular and the energy is delivered preferentially to a ventricular region of the heart.

3. A method as in claim 1, wherein the arrhythmia is atrial and the energy is delivered preferentially to an atrial region of the heart.

4. A method as in any one of claims 1–3, wherein delivery is performed by an implanted vibrational transducer.

5. A method as in claim 4, wherein the vibrational transducer is implanted at least partially under the patient's ribs.

6. A method as in claim 4, wherein the vibrational transducer is implanted at least partially in a gap between the patient's ribs.

7. A method as in claim 4, wherein the vibrational transducer is implanted at least partially over the patient's ribs.

8. A method as in claim 4, wherein the vibrational transducer is implanted in the abdominal region.

9. A method as in claim 4, wherein the vibrational transducer is implanted in a subcutaneous space of the anterior chest over the sternum.

10. A method as in claim 4, wherein the vibrational transducer is implanted in a subcutaneous space of the anterior chest over the ribs.

11. A method as in claim 4, wherein the vibrational transducer is implanted in a subcutaneous space of the posterior chest.

12. A method as in any one of claims 1–3, wherein delivery is performed with an external vibrational transducer.

13. A method as in claim 12, wherein the vibrational transducer is placed over the anterior chest.

14. A method as in claim 12, wherein the vibrational transducer is placed on the patient's back.

15. A method as in any one of claims 1–3, wherein delivering vibrational energy comprises sequentially energizing individual vibrational transducer segments, wherein at least some of the segments direct vibrational energy to different regions of the heart.

16. A method as in any one of claims 1–3, wherein delivering vibrational energy comprises sequentially energizing individual vibrational transducer segments, wherein at least some of the segments direct vibrational energy to the same region of the heart.

17. A method as in any one of claims 1–3, wherein the vibrational transducer consists essentially of a single piezoelectric disposed in a housing with an air backing.

18. A method as in claim 17, wherein the vibrational transducer comprises a piezo-composite material including piezo-electric ceramic posts in a polymer matrix.

19. A method as in any one of claims 1–3, wherein the vibrational energy is delivered to at least 50% of the heart.

20. A method as in any one of claims 1–3, wherein the vibrational energy is selectively delivered to less than 50% of the heart.

21. A system for stabilizing cardiac arrhythmias, said system comprising:
    a vibrational transducer implantable in a patient; and
    control circuitry for detecting an onset of an arrhythmia and activating the vibrational transducer to deliver controlled vibrational energy to the heart under conditions which terminate the arrhythmia, wherein the vibrational transducer comprises a piezo-composite material including piezo-electric ceramic posts in a polymer matrix.

22. A system as in claim 21, wherein the vibrational transducer and the control circuitry are packaged in a common housing.

23. A system as in claim 21, wherein the vibrational transducer and the control circuitry are packaged in separately implantable housings, further comprising a cable for connecting the housings.

24. A system as in any one of claims 21–23, wherein the vibrational transducer is adapted to deliver vibrational energy to at least 50% of the heart when implanted.

25. A system as in any one of claims 21–23, wherein the vibrational transducer is adapted to deliver energy to less than 50% of the heart when implanted.

26. A system as in any one of claims 21–23, wherein the control circuitry drives the vibrational transducer at a frequency in the range from 0.02 to 10 MHz, a burst length less than 5,000 cycles, a burst rate less than 100 kHz, a duty cycle less than 50%, a mechanical index less than 50, and a thermal index less than 4.

27. A system as in any one of claims 21–23, wherein the control circuitry comprises ECG elements for detecting the onset of an arrhythmia and for synchronizing the delivery of vibrational energy in response to such detection.

28. A system as in any one of claims 21–23, wherein the control circuitry comprises a power amplifier, an impedance matching circuit, and a signal generator, for each segment of the vibrational transducer.

29. A system as in any one of claims 21–23, wherein the control circuitry comprises a remotely rechargeable battery.

30. A system as in any one of claims 21–23, wherein the control circuitry comprises a transmitter andlor receiver for communication with an external controller.

31. A system as in any one of claims 21–23, wherein the control circuitry is adapted to detect ventricular fibrillation or ventricular tachycardia.

32. A system as in any one of claims 21–23, wherein the control circuitry is adapted to detect atrial fibrillation.

33. A system as in any one of claims 21–23, wherein the control circuitry is adapted to detect any rhythm having a rate below a programmed setting for the ventricles.

34. A system as in any one of claims 21–23, wherein the control circuitry is adapted to detect any rhythm having a rate below a programmed setting for the atria.

35. A system for stabilizing cardiac arrhythmias, said system comprising:

a vibrational transducer implantable in a patient; and control circuitry for detecting an onset of an arrhythmia and activating the vibrational transducer to deliver controlled vibrational energy to the heart under conditions which terminate the arrhythmia, wherein the vibrational transducer and the control circuitry are packaged in a common housing and the transducer consists essentially of a single piezo-electric disposed in the housing with an air backing.

36. A system as in claim 35, wherein the vibrational transducer is adapted to deliver vibrational energy to at least 50% of the heart when implanted.

37. A system as in claim 35, wherein the vibrational transducer is adapted to deliver energy to less than 50% of the heart when implanted.

38. A system as in claim 35, wherein the control circuitry drives the vibrational transducer at a frequency in the range from 0.02 to 10 MHz, a burst length less than 5,000 cycles, a burst rate less than 100 kHz, a duty cycle less than 50%, a mechanical index less than 50, and a thermal index less than 4.

39. A system as in claim 35, wherein the control circuitry comprises ECG elements for detecting the onset of an arrhythmia and for synchronizing the delivery of vibrational energy in response to such detection.

40. A system as in claim 35, wherein the control circuitry comprises a power amplifier, an impedance matching circuit, and a signal generator, for each segment of the vibrational transducer.

41. A system as in claim 35, wherein the control circuitry comprises a remotely rechargeable battery.

42. A system as in claim 35, wherein the control circuitry comprises a transmitter and/or receiver for communication with an external controller.

43. A system as in claim 35, wherein the control circuitry is adapted to detect ventricular fibrillation or ventricular tachycardia.

44. A system as in claim 35 wherein the control circuitry is adapted to detect atrial fibrillation.

45. A system as in claim 35, wherein the control circuitry is adapted to detect any rhythm having a rate below a programmed setting for the ventricles.

46. A system as in claim 35, wherein the control circuitry is adapted to detect any rhythm having a rate below a programmed setting for the atria.

* * * * *